United States Patent [19]

Schroeder et al.

[11] Patent Number: 5,110,928

[45] Date of Patent: May 5, 1992

[54] PREPARATION OF N-ARYL-SUBSTITUTED 2-AMINOALKYL-2-HYDROXYALKYLAMINES AND N-ARYL-SUBSTITUTED PIPERAZINES

[75] Inventors: Wolfgang Schroeder, Bad Durkheim; Guenther Ruider, Wachenheim, both of Fed. Rep. of Germany

[73] Assignee: BASF Aktiengesellschaft, Ludwigshafen, Fed. Rep. of Germany

[21] Appl. No.: 670,042

[22] Filed: Mar. 15, 1991

[30] Foreign Application Priority Data

Mar. 15, 1990 [DE] Fed. Rep. of Germany ........ 4008322

[51] Int. Cl.$^5$ ................... C07D 295/02; C07D 295/08
[52] U.S. Cl. ................................ 544/395; 544/392; 544/394; 564/395; 564/401; 564/402
[58] Field of Search ............... 544/392, 394, 395; 564/401, 395, 402

[56] References Cited

U.S. PATENT DOCUMENTS

| | | | |
|---|---|---|---|
| 4,774,336 | 9/1988 | Su | 544/392 |
| 4,827,035 | 5/1989 | Mueller et al. | 544/402 |
| 4,845,218 | 7/1989 | Schroeder | 544/404 |
| 4,888,447 | 12/1989 | Smith | 544/401 |

FOREIGN PATENT DOCUMENTS

| | | |
|---|---|---|
| 1186069 | 1/1965 | Fed. Rep. of Germany . |
| 2624042 | 12/1976 | Fed. Rep. of Germany . |
| 3605005 | 8/1987 | Fed. Rep. of Germany . |
| 1186341 | 8/1959 | France . |
| 1575059 | 7/1969 | France . |
| 902570 | 8/1962 | United Kingdom . |
| 1491390 | 11/1977 | United Kingdom . |

OTHER PUBLICATIONS

Schroeder, CA107-156377S (1987).

Hartof et al., CA 105-153081p (1986).
Houben-Weyl, vol. XI/1, pp. 126 ff. (1957).
Yuki Gosei Kagaku Kyokai Ski, vol. 17, pp. 17 ff. (1959).
Nippon Kagaku Zasshi, vol. 89, p. 408 (1968).

*Primary Examiner*—Cecilia Shen
*Attorney, Agent, or Firm*—John H. Shurtleff

[57] ABSTRACT

N-Aryl-substituted 2-amino-alkyl-2-hydroxyalkylamines and N-aryl-substituted piperazines Ia and Ib respectively

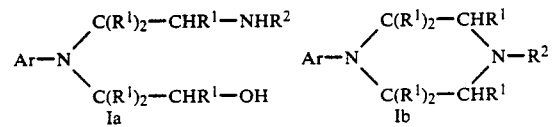

(Ar=aryl; R$^1$=hydrogen, methyl, identical or different, R$^2$=hydrogen, alkyl) are prepared by reacting an N,N-di(2-hydroxyalkyl)-N-arylamine II

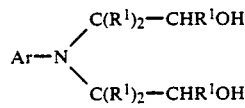

with ammonia or a primary amine III $H_2N\text{-}R^2$  III at elevated temperature and under elevated pressure in the presence of hydrogen and of a catalyst which is a supported catalyst whose active mass predominantly contains copper and/or nickel and/or cobalt in the form of the metal or an oxide.

8 Claims, No Drawings

PREPARATION OF N-ARYL-SUBSTITUTED 2-AMINOALKYL-2-HYDROXYALKYLAMINES AND N-ARYL-SUBSTITUTED PIPERAZINES

The present invention relates to an improved process for preparing N-aryl-substituted 2-aminoalkyl-2-hydroxyalkylamines and N-aryl-substituted piperazines of the formulae Ia and Ib respectively

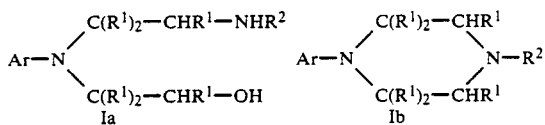

where Ar is aryl, the $R^1$ radicals can be identical or different and are hydrogen or methyl, and $R^2$ is hydrogen or alkyl, by reacting an N,N-di(2-hydroxyalkyl)-N-arylamine of the formula II

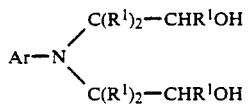

with ammonia or a primary amine of the formula III

 III at elevated temperature and under elevated pressure in the presence of hydrogen and of a catalyst.

The synthesis of piperazines by reacting diethanolamines with ammonia or primary amines on hydrogenation catalysts is known (see Houben-Weyl, Vol. XI/1, pages 126 ff, Thieme-Verlag, Stuttgart, 1957). DE-A-36 05 005 specifically describes the synthesis of N-methylpiperazine from diethanolamine and methylamine in the presence of hydrogen and copper-containing catalysts. Other N-substituted piperazines which are described, for example, in DE-A-26 24 042 have to date been obtainable only in moderate yields.

Compounds Ib have been prepared to date only in low yields by reductive ammonolysis (see Yuki Gosei Kagaku Kyokai Ski 17 (1959) 17) or by condensation of aminoalkyl esters with imides (see Nippon Kagaku Zasshi 89 (1968) 408).

It is an object of the present invention to provide a process for preparing N-aryl-substituted 2-aminoalkyl-2-hydroxyalkylamines Ia and N-aryl-substituted piperazines Ib which makes compounds Ia and Ib available in higher yields and with higher selectivity than hitherto.

We have found that this object is achieved by a process for preparing N-aryl-substituted 2-aminoalkyl-2-hydroxyalkylamines and N-aryl-substituted piperazines of the formulae Ia and Ib respectively

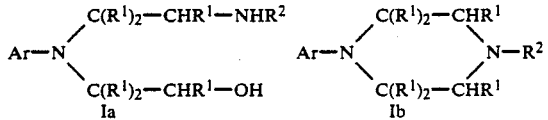

where Ar is aryl, the $R^1$ radicals can be identical or different and are hydrogen or methyl, and $R^2$ is hydrogen or alkyl, by reacting an N,N-di(2-hydroxyalkyl)-N-arylamine of the formula II

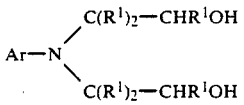

with ammonia or a primary amine of the formula III

 III at elevated temperature and under elevated pressure in the presence of hydrogen and of a catalyst, which comprises using for this a supported catalyst whose active mass contains predominant amounts of copper and/or nickel and/or cobalt in the form of the metal or an oxide.

Findings to date indicate that the nature of Ar, $R^1$ and $R^2$ has, in principle, no effect on the novel process as long as they have no substituents which react under the conditions of the reaction.

Suitable for Ar are 1- or 2-naphthyl and, in particular, phenyl, which are unsubstituted or substituted once, twice or three times by hydroxyl or $C_1$-$C_4$-alkyl, such as 2-, 3- and 4-hydroxyphenyl, 2-, 3- and 4-methylphenyl, 2,4,6-trimethylphenyl, 4-isopropylphenyl, 4-tert-butylphenyl, 2-methyl-1-naphthyl and 4-methyl-1-naphthyl.

The $R^1$ radicals, which can be identical or different, are hydrogen or methyl, with hydrogen being preferred.

Suitable for $R^2$ are hydrogen, $C_1$-$C_8$-alkyl, especially methyl, ethyl, i-propyl and tert-butyl, $C_3$-$C_8$-cycloalkyl such as cyclopropyl, cyclopentyl and, preferably, cyclohexyl.

The active mass of the catalysts to be used according to the invention either consists of a copper oxide, a cobalt oxide or nickel oxide or mixtures of these oxides alone or it predominantly contains them, i.e. in proportions of at least 50, preferably 90, % by weight, in addition to other components, for example trimanganese tetroxide, molybdenum trioxide, manganese(II) oxide, phosphoric acid, and chromium, ruthenium, silver or palladium as metals or as oxides.

Particularly suitable carrier materials are oxides which are not reduced under the reaction conditions, such as alumina, silica, titania and zirconia, and aluminum silicates and mixtures of these materials.

The supported catalysts can be obtained in a conventional manner, e.g. by suspending the carrier material in an aqueous solution of the salts of the metals from which the active oxides are derived, e.g. the nitrates or acetates, and adding alkali metal carbonates or bicarbonates to the suspension, when the carbonates or bicarbonates of the metals of the active mass are precipitated on the carrier particles. The solid is then separated off, dried and heated at 350°-600° C. in a stream of air, when the carbonates or bicarbonates are converted into the oxides.

The resulting mass can, after subsequent grinding and screening to a suitable particle size distribution, e.g. to diameters of from 50 to 300μ, be used and/or compressed by conventional methods to give rings, tablets or beads and employed as fixed catalyst.

During or, preferably, before the reaction, the oxide masses are converted into the active form by reduction with hydrogen. In the pretreatment, a mixture of 5-20% by volume hydrogen and 80-95% by volume nitrogen is passed over the catalyst initially at 120°–160° C. for from 4 to 10 hours, after which it is heated over the course of from 3 to 5 hours to 160°–200° C. and the reduction is continued for a further 3 to 5 hours. Finally, the nitrogen is replaced by hydrogen, and the temperature is raised to 250°–300° C. The reduction is complete after a further 6 to 10 hours.

The amount of the catalyst is expediently from 1 to 100 g of active mass per mole of dihydroxy compound II employed.

The reaction is preferably carried out in such a way that the catalyst is suspended in the liquid phase containing the reactants or the reactants are passed in liquid phase over a fixed catalyst bed.

The molar ratio of the starting compounds ammonia or amine III to dihydroxyalkylamine II is preferably from 1:1 to 150:1.

It is technically advantageous to take up the solid and liquid starting compounds II and III in solvents which are inert under the reaction conditions. Particularly suitable for this are tetrahydrofuran, dioxane, ethylene glycol dimethyl ether or N-methylpyrrolidone in amounts of from 0.5 to 2 kg per kg of starting materials II and III.

Starting compounds III which are gaseous under normal conditions are preferably fed into the reactor in liquid phase without solvent under pressure.

It is essential for the selectivity and activity of the catalyst to carry out the reaction in the presence of hydrogen. The total pressure, comprising the partial pressures of the starting compounds, of the solvent (if present) and of the hydrogen, is preferably in the range from 40 to 400 bar, preferably from 100 to 300 bar, with the partial pressure of hydrogen being 80 to 90% thereof.

The temperature range for the formation of the products Ia and Ib is from 100° to 300° C., preferably from 160° to 245° C.

The ratio of Ia to Ib in the product can preferably be controlled by the choice of temperature and of catalyst system. Thus, for a defined catalyst composition, the piperazines Ib are usually formed preferentially at temperatures which are 20° to 40° C. higher than those used for synthesizing the corresponding amines Ia.

If, on the other hand, no oxides which cannot be reduced under the conditions are employed as carrier material there is preferential formation of the 2-aminoalkyl-2-hydroxyalkylamines Ia irrespective of the chosen temperature in the stated range (see Examples).

The process can be carried out continuously or batchwise, and in the latter case the reaction takes from 0.02 to 1 h.

The crude product is purified in a conventional manner, such as by fractional distillation or crystallization.

The compounds I are important starting materials for preparing psychotropic drugs such as tranquilizers, neuroleptics or analgesics (Coll. Czech. Chem. Comm. 40 (1975) 1204, 1612, EP-B-190 472) and cosmetics and photochemicals. They are also used in the human and animal food industries (DE-A-26 24 042). Some of the compounds Ia are also employed in analysis for quantitative determination of $H_2O_2$ (JP-A-60241899).

EXAMPLES

A Composition of the catalysts used

TABLE 1

| | Catalyst compositions Catalyst [% by weight] | | | | | |
|---|---|---|---|---|---|---|
| | A | B | C | D | E | F |
| Active mass | | | | | | |
| Cobalt (II) oxide | 10 | 10 | 16 | — | — | 66 |
| Nickel (II) oxide | 10 | 10 | — | 26 | — | — |
| Copper (II) oxide | 4 | 4 | — | 9 | — | 20 |
| Copper | — | — | — | — | 44 | — |
| Trimanganese tetroxide | — | — | — | 2.5 | — | 7 |
| Molybdenum trioxide | — | — | — | — | — | 4 |
| Phosphoric acid | — | — | — | — | — | 3 |
| Carrier material | | | | | | |
| Alumina | — | — | 83 | — | 56 | — |
| Silica | — | 76 | — | 62.5 | — | — |
| Zirconia | 76 | — | — | — | — | — |
| Manganese (II) oxide | — | — | 1 | — | — | — |

B Reactions

The experiments were carried out in a continuous process in which a tube reactor with a capacity of 5 l was 60% filled with catalyst. The catalyst comprised the mixtures described under A which had been compressed to cylindrical tablets (height = diameter = 4 mm). The reactor was flushed with hydrogen and then heated to the reaction temperature, and then the starting materials were fed in. The reaction was carried out under 250 bar which was reached by injecting hydrogen. The reaction mixture leaving the reactor was cooled, returned to atmospheric pressure and fractionally distilled. An exception to this was the product from Experiment 7 (4-hydroxyphenylpiperazine) which was purified not by distillation but by crystallization from tetrahydrofuran. The products were always obtained more than 99% pure. The yields were determined, and the products were analyzed, by conventional methods such as GC and NMR.

In Experiments 1 to 6 and 9, the dihydroxyalkylamine II was fed into the reactor at 1.5 mol/h as a 1.5 molar tetrahydrofuran solution at the same time as liquid ammonia (120 mol/h).

In Experiment 7, 1.2 mol/h dihydroxy amine II was employed as a 1.2 molar solution in N-methylpyrrolidone with 120 mol/h liquid ammonia.

In Experiment 8, 4.9 mol/h dihydroxy amine III and 15.1 mol/h isopropylamine were employed in a solution composed of 4.9 mol of dihydroxy amine III and 15.1 mol of isopropylamine per 1 of tetrahydrofuran.

Further details on the experiments and the results are given in Table 2.

TABLE 2

| | | | | Experimental results | | | |
|---|---|---|---|---|---|---|---|
| Example No. | Catalyst | $ArN(CH_2CH_2OH)_2$ II Ar | $H_2NR^2$ $R^2$ | Temperature [°C.] | Conversion [%] | Product | Yield [%] |
| 1 | A | Phenyl | H | 180 | 100 | N-Phenylpiperazine Ib | 75 |
| 2 | B | Phenyl | H | 180 | 100 | N-Phenylpiperazine Ib | 75 |
| 3 | C | Phenyl | H | 190 | 100 | N-Phenylpiperazine Ib | 70 |
| 4 | D | Phenyl | H | 180 | 100 | N-Phenylpiperazine Ib N-(2-aminoethyl)-N-(2-hydroxyethyl)aniline Ia | 8 60 |
| 5 | D | Phenyl | H | 220 | 100 | N-Phenylpiperazine Ib | 55 |

TABLE 2-continued

| Example No. | Catalyst | ArN(CH₂CH₂OH)₂ II Ar | H₂NR² R² | Temperature [°C.] | Conversion [%] | Product | Yield [%] |
|---|---|---|---|---|---|---|---|
| | | | | | | N-(2-aminoethyl)-N-(2-hydroxyethyl)aniline Ia | 1 |
| 6 | A | 2-Tolyl | H | 180 | 100 | N-o-Tolylpiperazine Ib | 70 |
| 7[1] | A | 4-Hydroxyphenyl | H | 180 | 100 | N-(p-Hydroxyphenyl)-piperazine Ib | 65 |
| 8 | E | Phenyl | iPr | 200 | 98 | N-Isopropyl-N'-phenyl-piperazine Ib | 65 |
| 9 | F | Phenyl | H | 180 | 60 | N-Phenylpiperazine Ib | 20 |
| | | | | | | N-(2-aminoethyl)-N-(2-hydroxyethyl)aniline Ia | 75 |

[1] in N-methylpyrrolidone

We claim:

1. A process for preparing N-aryl-substituted 2-aminoalkyl-2-hydroxyalkylamines and N-aryl-substituted piperazines of the formulae Ia and Ib respectively

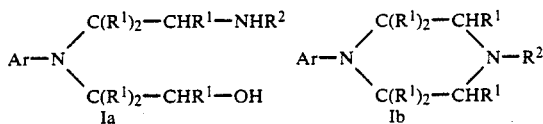

where Ar is aryl, the R¹ radicals can be identical or different and are hydrogen or methyl, and R² is hydrogen or alkyl, by reacting an N,N-di(2-hydroxyalkyl)-N-arylamine of the formula II

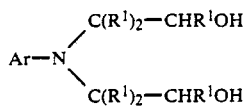

with ammonia or a primary amine of the formula III

   III at elevated temperature and under elevated pressure in the presence of hydrogen and of a catalyst, which comprises using for this a supported catalyst whose active mass contains predominant amounts of copper and/or nickel and/or cobalt in the form of the metal or an oxide.

2. A process as claimed in claim 1, wherein the catalyst carrier material is composed of alumina, silica, zirconia, titania, aluminum silicates or mixtures thereof.

3. A process as claimed in claim 1, wherein the active mass of the catalyst contains at least 90% by weight of the members selected from the group consisting of copper, nickel, cobalt, their oxides and mixtures thereof.

4. A process as claimed in claim 1, wherein R¹ represents hydrogen or methyl, R² represents hydrogen, $C_1$–$C_8$-alkyl or $C_3$–$C_8$-cycloalkyl, and aryl represents phenyl, 1-naphthyl or 2-naphthyl, each aryl being unsubstituted or substituted from one to three times by hydroxy or $C_1$–$C_4$-alkyl.

5. A process as claimed in claim 1, wherein the reaction is carried out at a temperature of from 100° to 300° C. and under a total pressure of about 40 to 400 bar.

6. A process as claimed in claim 5, wherein the hydrogen has a partial pressure of about 80 to 90% of the total pressure.

7. A process as claimed in claim 5, wherein the reaction is carried out in an inert liquid solvent with a molar ratio of said ammonia or amine III to the dihydroxyalkylamine II of about 1:1 to 150:1.

8. A process as claimed in claim 7, wherein the inert solvent is selected from the group consisting of tetrahydrofuran, dioxane, ethylene glycol dimethyl ether and N-methylpyrrolidone.

* * * * *

UNITED STATES PATENT AND TRADEMARK OFFICE
CERTIFICATE OF CORRECTION

PATENT NO. : 5,110,928
DATED : May 5, 1992
INVENTOR(S) : Wolfgang Schroeder and Guenther Ruider It is certified that error appears in the above-identified patent and that said Letters Patent is hereby corrected as shown below:

Claim 1, in column 5, line 30: cancel "by" and substitute --which comprises--.

Claim 1, in column 5, lines 44-45: cancel "of a catalyst, which comprises using for this".

Signed and Sealed this

Twenty-ninth Day of June, 1993

*Attest:*

MICHAEL K. KIRK

*Attesting Officer*     *Acting Commissioner of Patents and Trademarks*